United States Patent [19]

Fleury

[11] Patent Number: 4,990,145

[45] Date of Patent: Feb. 5, 1991

[54] DISPOSABLE BAG WITH HAND PROTECTION

[75] Inventor: Richard L. Fleury, Chicago, Ill.

[73] Assignee: GKR Industries, Inc., Alsip, Ill.

[21] Appl. No.: 306,501

[22] Filed: Feb. 7, 1989

[51] Int. Cl.[5] .................... A61M 1/00

[52] U.S. Cl. .................... 604/317

[58] Field of Search ........ 604/317, 322, 323, 327–329, 604/346–348, 355; 383/36; 4/144.2, 144.3; 294/1.3

[56] References Cited

U.S. PATENT DOCUMENTS 3,797,734 3/1974 Fleury .................... 383/36
4,741,565 5/1988 Bagg .................... 294/1.3
4,768,818 9/1988 Kolic .................... 294/1.3

FOREIGN PATENT DOCUMENTS 2936622 3/1981 Fed. Rep. of Germany ....... 4/144.2

*Primary Examiner*—David J. Isabella
*Attorney, Agent, or Firm*—Baker & McKenzie

[57] ABSTRACT

The invention relates to a container for vomit or urine. The container includes a flattened conical paperboard funnel to which is sealably attached a bag. The funnel has a "duck-bill" valve attached to its lower end, and the valve is disposed inside the bag. A shroud or cover is sealingly attached to the outer surface of the funnel. The cover is shaped to allow easy insertion of the user's hand while providing protection for the user from contact with material which may miss the funnel during initial positioning thereof.

18 Claims, 1 Drawing Sheet

DISPOSABLE BAG WITH HAND PROTECTION

BACKGROUND AND SUMMARY OF THE INVENTION

The present invention relates to containers for receiving body fluids, such as vomit and urine, and in particular, to disposable containers which are collapsible which provide sanitary protection to the user.

U.S. Pat. No. 3,797,734 (the '734 patent) shows a disposable bag of the type with which the present invention is intended to be used. The '734 patent shows a bag having a paperboard funnel sealingly engaging a plastic bag. The upper rim of the bag is attached to the middle of the outside surface of the funnel. The bottom portion of the funnel contains a simple valve comprised of a flattenable plastic tube which allows entry of fluid through the funnel into the bag, but which prevents fluid from escaping the bag. products made in accordance with the '734 patent have been sold in substantial numbers.

Disposable containers are used in a variety of applications. On airplanes and other transportation vehicles, they provide means to assist those who may suffer from motion sickness. There is also a need in hospitals for simple, portable receptacles for vomit and urine.

However, prior art devices for this purpose have, to some extent, needed improvement in that the user's hand is generally exposed to the regurgitated fluid which may miss entry into the container. This problem is particularly prevalent in situations where a person is vomiting. Vomiting is usually accompanied by large convulsive bodily movement, and the person vomiting generally finds it difficult to hold still. It may also be difficult for the person vomiting to control arm and hand movement during actual regurgitation. Therefore, there is a likelihood that at least some of the regurgitated substance will miss any receptacle held by the person vomiting.

Likewise, if another individual assists the person vomiting, it will be difficult to maintain alignment of the container in the proper position to completely prevent any spillage. This difficulty is again due to the large convulsive movements which normally accompany vomiting.

It is important to prevent regurgitated or urinated fluid from contacting the user's skin because such fluid will often contain infectious or contagious agents such as viruses and bacteria.

It is therefore an object of the present invention to provide a container for receiving body fluids which will protect the user from spillage.

Another object of the present invention is to provide a container which can help prevent the spreading of infectious or contagious diseases.

Another object of the present invention is to provide a disposable, collapsible bag which will protect the user's hand from coming into contact with fluids to be contained therein.

A further object of the present invention is to provide a disposable, collapsible bag for receiving vomit and urine which has integral hand protection.

Yet another object of the present invention is to provide a simple and economical container for receiving vomit and urine.

These and other objects of the invention are achieved with a container comprised of a paperboard funnel to which is sealingly attached a flat plastic bag. The bag is attached to the outer surface of the funnel. A simple duck-bill valve is attached to the lower portion of the funnel which lies inside the bag. The valve is arranged to allow flow of material into the bag, but prevent escape therefrom. A hand cover is sealingly attached to the outer surface of the funnel at a level which allows a user's hand to grasp the funnel.

Further objects and advantages of the present invention will become apparent upon a reading of the following specification, read in conjunction with the attached drawings.

DETAILED DESCRIPTION OF THE INVENTION

Figure 1:
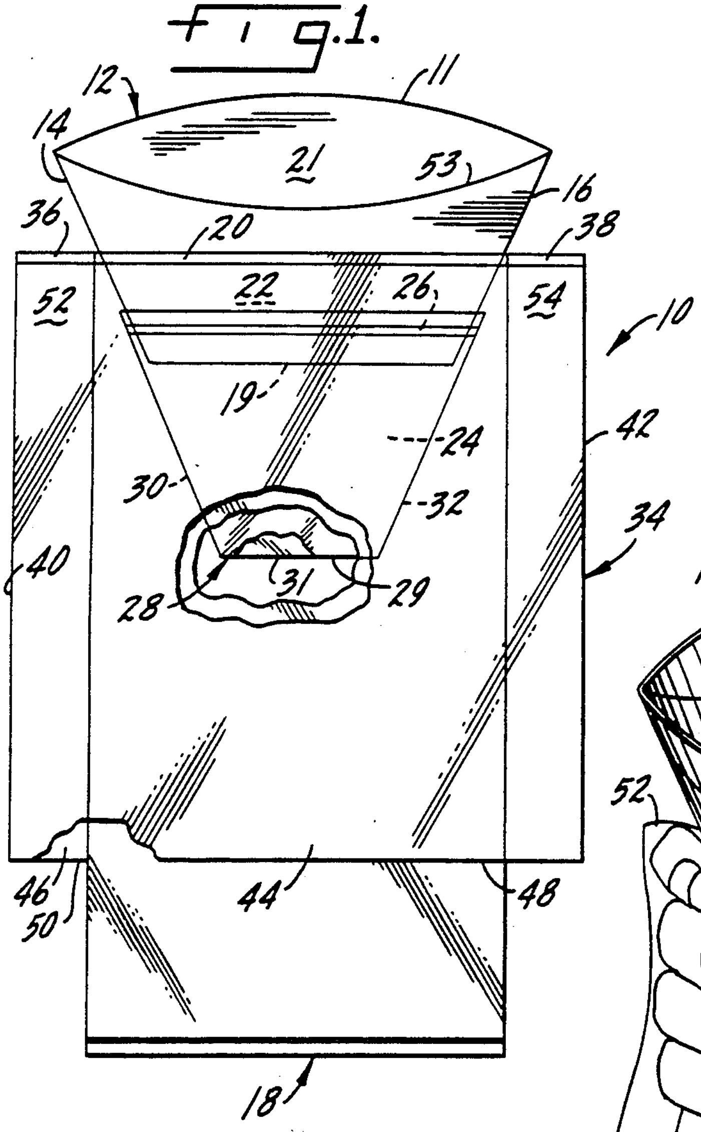
FIG. 1 is an elevational view of a container made in accordance with the present invention.

FIG. 1 shows the main components of a container 10 of the present invention in a flat, but unfolded condition. A flattened, generally trapezoidal funnel 12 has an arched top 11 and sloping edges 14 and 16. A plastic bag 18 is sealingly attached to the funnel 12 along front seal line 20 and rear seal line (not shown).

Inside the bag 18 and attached to a lower part 22 of the funnel is a valve 24. The valve 24 has a top sealingly attached to the periphery of the lower part 22 along the front seal line 26 and the rear seal line (not shown). The valve is a very flexible element with an open bottom 28 through which material can enter the bag 18, but through which material cannot exit the bag 18. The valve 24 has sloping sides 30 and 32 which have generally the sam slope as the sides 14 and 16 of the funnel 12. The valve operates as a kind of "duck-bill" valve, since the bottom edges 29 and 31 of the open end 28 tend to close off the opening in the end of the valve, due to the flexible nature of the material comprising the valve.

A shroud 34 covers a major portion of the exterior of the container 10. Seal lines 36 and 38 are extensions of seal line 20, and together with the closed edges 40 and 42 make the cover 34 sealed on three of its four sides. The cover 34 is comprised of front and back sheets 44 and 46 respectively which are unattached at their bottom edges 48 and 50. The cover 34 is substantially wider than the bag 18 to provide upper corners 52 and 54, which provide access for a user's hand to operate the funnel.

Figure 2:
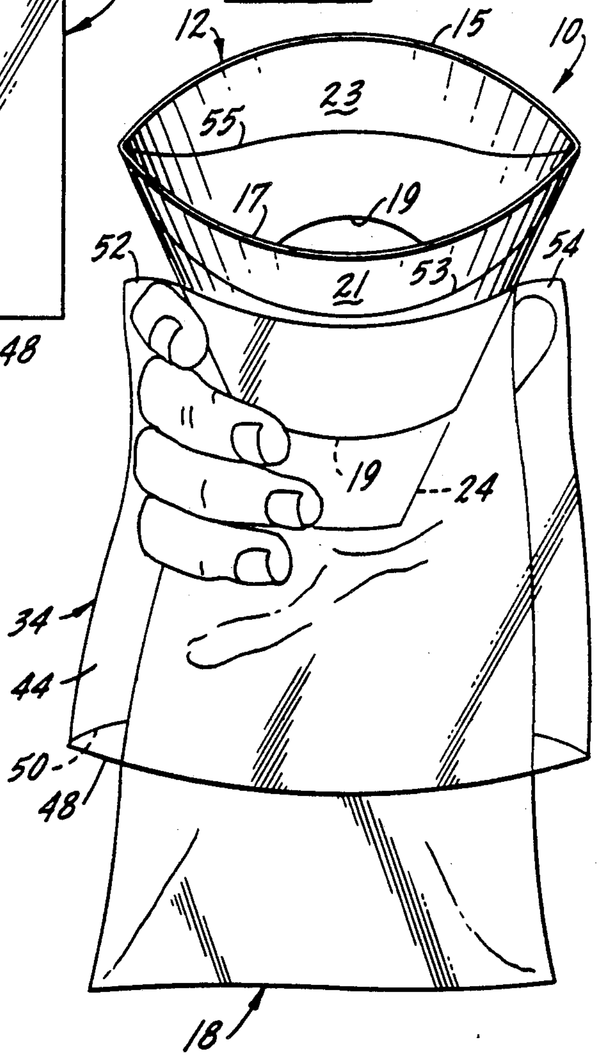
FIG. 2 is a perspective view of a container made in accordance with the present invention, with a user's hand shown holding the container.

The perspective view in FIG. 2 shows how a user operates the container of the present invention. The user's hand is inserted between the sheets 44 and 46. A thumb is positioned in one of the upper corners, 54 for example, and a user's finger, preferably the index finger, is placed in the upper corner 52. The user then applies lateral pressure to the edges 14 and 16 of the funnel which causes the funnel to open both at its upper edges 15 and 17, and at its bottom 19.

The funnel has the shape of a truncated cone when it is in a fully open position. However, the funnel is made of a resilient paperboard which is creased at the edges 14 and 16. The creased edges allow the container to be folded neatly and flatly. The paperboard is heavy enough and the creases are formed so that the funnel tends to return to the flat position shown in FIG. 1.

The shroud 34 is long enough and wide enough to completely cover even a large sized human hand. In a preferred embodiment, the sealing lines 36 and 38 are about an inch (2.54 cm) in length to allow room for fingers and thumb. The overall flattened dimension of the shroud or cover 34 is preferably about 8.5 inches (21.6 cm). However, the sealing line extensions 36 and 38 could be as short as about 0.5 inches (1.3 cm) and as long as about 2.0 inches (5.1 cm) or longer, and the length of the cover could be as short as about 5 inches (12.7 cm) and as long as 10 inches (25.4 cm) or longer. Its length also provides protection for a user's wrist and shirt cuff. However, its length is short enough to allow quick and simple insertion of a hand to the use position shown in FIG. 2.

After vomiting is completed, the foldable covers 21 and 23 can be pushed inwardly and folded along score line 53 and 55 to cover any residual material which may be adhering to the inside portion of the funnel. Once the foldable covers 21 and 23 are in the closed position, the arcuate shape of the score lines 53 and 55 and the resilience of the funnel tend to maintain the foldable covers 21 and 23 in the closed position. Also, with the covers 21 and 23 in the closed position, the bottom edges 29 and 31 of the valve 24 can easily contact one another to make the valve fully operable to prevent escape of material from the bag 18.

It should be noted that the bag can be easily operated to prevent any contact between the hand of the one holding the container and the fluid entering the bag. This is an important aspect of the invention, since infectious and contagious agents may be present in both vomit and urine. The likelihood of such agents being passed is greatly reduced if the vomit or urine is prevented from making contact with the skin of the person holding the container. The present invention is specially designed to prevent such contact from the time the container is initially used until disposal thereof.

It should be noted that for purposes of ease of illustration, the bag 18 and cover 34 are shown as being made of clear plastic. Clear plastic is preferred for hospital use where viewing of the contents may be required by a doctor. Such viewing may be required to measure the amount of vomit or urine, or to determine the color or other physical property of the substance contained in the bag 18. However, for uses on airplanes and the like, an opaque bag may be preferred so that the contents of the bag cannot be seen. Viewing of the contents could be unsettling to other passengers. In either application, the cover 34 is preferably clear plastic to facilitate proper placement of fingers and thumb on the edges of the funnel and the subsequent spreading or opening of the funnel from its flat to its generally conical shape.

While a specific embodiment of the invention has been shown and described, it will be apparent to those skilled in the art that numerous alternatives, modifications, and variations of the embodiment shown can be made without departing from the spirit and scope of the appended claims.

I claim:

1. In a disposable device for capturing body fluids wherein said device includes a flexible, foldable, bag-like container section open at one end, a resiliently flexible, openable and collapsible funnel-shaped upper member, the open end of said container section being sealingly attached to an outer surface of said upper member, and valve element sealingly attached to a lower end of said upper member, said valve element being a generally tubular flexible member extending into said container section, the improvement comprising: a protective generally tubular flexible cover attached to an upper outer surface of said device, one end of said cover being sealingly attached to said upper outer surface to allow opening and closing of said upper member from within said cover, the other end of said cover having a length and inside lateral dimension sufficient to cover a user's hand while said hand holds said funnel-shaped upper member.

2. A device for capturing body fluids in accordance with claim 1 wherein:

said cover has a lateral dimension substantially greater than said bag-like container.

3. A device for capturing body fluids in accordance with claim 1 wherein:

said cover is heat sealed to said funnel-shaped upper member.

4. A device for capturing body fluids in accordance with claim 1 wherein:

said cover and said bag-like container are heat sealed to said funnel-shaped upper member at substantially the same location.

5. A device for capturing body fluids in accordance with claim 1 wherein:

said cover is made of clear plastic.

6. A device for capturing body fluids in accordance with claim 1 wherein:

said cover is wider than said funnel-shaped upper member at the point of attachment between said funnel-shaped upper member and said cover.

7. A device for capturing body fluids in accordance with claim 1 wherein:

said cover has a generally constant lateral dimension through its length.

8. A device for capturing body fluids comprising a bag-like container, a funnel-shaped upper member sealingly attached to said bag-like container, and a cover attached to said device for covering a user's hand during use of said device, said cover and said bag-like container being heat sealed to said funnel-shaped upper member at substantially the same location.

9. A device for capturing body fluids in accordance with claim 8 wherein:

said cover has a lateral dimension substantially greater than said bag-like container.

10. A device for capturing body fluids in accordance with claim 8 wherein:

said cover is heat sealed to said funnel-shaped upper member.

11. A device for capturing body fluids in accordance with claim 8 wherein:

said cover is made of clear plastic.

12. A device for capturing body fluids in accordance with claim 8 wherein:

said cover is wider than said funnel-shaped upper member at the point of attachment between said funnel-shaped upper member and said cover.

13. A device for capturing body fluids in accordance with claim 8 wherein:

said cover has a generally constant lateral dimension throughout its length.

14. In a disposable device for capturing body fluids wherein said device includes a flexible, foldable, bag-like container section open at one end, a resiliently flexible openable and collapsible funnel-shaped upper member, the open end of said container section being sealingly attached to an outer surface of said upper member, the improvement comprising: a protective generally tubular flexible cover attached to an upper outer surface of said device, one end of said cover being sealingly attached to said upper outer surface to allow opening and closing of said upper member from within said cover, the other end of said cover having a length and inside lateral dimension sufficient to cover a user's hand while said hand holds said funnel-shaped upper member.

15. A device for capturing body fluids in accordance with claim 14 wherein:

said cover has a lateral dimension substantially greater than said bag-like container.

16. A device for capturing body fluids in accordance with claim 14 wherein:

said cover is heat sealed to said funnel-shaped upper member.

17. A device for capturing body fluids in accordance with claim 14 wherein:

said cover and said bag-like container are heat sealed to said funnel-shaped upper member at substantially the same location.

18. A device for capturing body fluids in accordance with claim 14 wherein:

said cover is wider than said funnel-shaped upper member at the point of attachment between said funnel-shaped upper member and said cover.

* * * * *